US008481529B2

(12) United States Patent
Hurley et al.

(10) Patent No.: US 8,481,529 B2
(45) Date of Patent: Jul. 9, 2013

(54) COMBINATION CANCER CHEMOTHERAPY

(75) Inventors: Laurence H. Hurley, Tucson, AZ (US); Mary Guzman, Tucson, AZ (US)

(73) Assignee: The Arizona Board of Regents on Behalf of the University of Arizona, Tucson, AZ (US)

(*) Notice: Subject to any disclaimer, the term of this patent is extended or adjusted under 35 U.S.C. 154(b) by 388 days.

(21) Appl. No.: 12/301,217

(22) PCT Filed: May 9, 2007

(86) PCT No.: PCT/US2007/068601
§ 371 (c)(1),
(2), (4) Date: May 21, 2009

(87) PCT Pub. No.: WO2007/137000
PCT Pub. Date: Nov. 29, 2007

(65) Prior Publication Data
US 2009/0270377 A1 Oct. 29, 2009

Related U.S. Application Data

(60) Provisional application No. 60/800,824, filed on May 16, 2006.

(51) Int. Cl.
*A61K 31/535* (2006.01)

(52) U.S. Cl.
USPC ..................................... 514/229.5

(58) Field of Classification Search
USPC ..................................... 514/229.5
See application file for complete search history.

(56) References Cited

U.S. PATENT DOCUMENTS

| 5,756,510 | A | * | 5/1998 | Griffin et al. ............ 514/263.1 |
| 6,156,763 | A | | 12/2000 | Kerwin et al. |
| 6,331,396 | B1 | | 12/2001 | Silverman et al. |
| 7,141,565 | B1 | | 11/2006 | Whitten et al. |
| 7,163,548 | B2 | | 1/2007 | Stulen et al. |
| 7,326,702 | B2 | | 2/2008 | Whitten et al. |
| 7,354,916 | B2 | | 4/2008 | Whitten et al. |
| 7,381,720 | B2 | | 6/2008 | Whitten et al. |
| 2005/0085468 | A1 | | 4/2005 | Whitten et al. |
| 2005/0187176 | A1 | | 8/2005 | Bates et al. |
| 2006/0029950 | A1 | | 2/2006 | Whitten et al. |

FOREIGN PATENT DOCUMENTS

| WO | WO 00/61597 | 10/2000 |
| WO | WO 2004/036188 | 4/2004 |
| WO | WO 2005/035579 | 4/2005 |
| WO | WO 2005/037997 | 4/2005 |
| WO | WO 2005/049867 | 6/2005 |
| WO | WO 2006/050026 | 5/2006 |

OTHER PUBLICATIONS

Berenbaum (Pharmacological Reviews, 1989, 93-141.*

Bowman et al. (2001) "Differential Effects of the Poly (ADP-ribose) Polymerase (PARP) Inhibitor NU1025 on Topoisomerase I and II Inhibitor Cytotoxicity in L1210 Cells in Vitro," *Brit J. Cancer* 84:106-112.
Cepeda et al. (Jan. 2006) "Poly(ADP-Ribose) Polymerase-1 (PARP-1) Inhibitors in Cancer Chemotherapy," *Recent Patents on Anti-Cancer Drug Disc.* 1:39-53.
Đapić et al. (2003) "Biophysical and Biological Properties of Quadruplex Oligodeoxyribonucleotides," *Nuc. Acids Res.* 31(8):2097-2107.
Guilford Pharmaceuticals Inc. (Apr. 1, 2004) "Guilford Presents Novel Research at the 95th Annual Meeting of the American Association for Cancer Research," New Release.
Hurley et al. (Aug. 2006) "Drug Targeting of the c-MYC Promoter to Repress Gene Expression Via a G-Quadruplex Silencer Element," *Sem. Oncol.* 33(4):498-512.
International Search Report and Written Opinion Corresponding to International Application No. PCT/US2007/068601, Mailed Jan. 17, 2008.
Jagtap et al. (May 2005) "Poly(ADP-Ribose) Polymerase and Therapeutic Effects of its Inhibitors," *Nat. Rev. Drug Disc.* 4:421-440.
Jin et al. (2004) "In Vivo Efficacy of CX-3543, a Novel c-Myc Oncogene Inhibitor," *Proc. Ann. Meet. Am. Assoc. Cancer. Res.* 45:LB-243, Abstract.
Khurts et al. (Dec. 3, 2004) "Nucleolin Interacts with Telomerase," *J. Biol. Chem.* 279(49):51508-51515.
Lim et al. (2005) "Clinical Development of CX-3543, a novel Multi-Targeting Antitumor Agent," *J. Clin. Oncol.* 2005 ASCO Annual Meeting Proceedings, Part 1, 23(16S):3206, Jun. 1 Supplement.
Liu et al. (2005) "Binding of G-Quadruplex-Interactive Agents to Distinct G-Quadruplexes Induces Different Biological Effects in MiaPaCa Cells," *Nucleosides Nucleotides Nucleic Acids* 24(10-12):1801-1815.
Marschke et al. (Jun. 20, 2006) "Phase I Clinical Trial of CX-3543, a Pro-Apoptotic Antitumor Agent," *J. Clin. Oncol.* 2006 ASCO Annual Meeting Proceedings Part I., 24(18S): Abstract 3082.
Mi et al. (Mar. 7, 2003) "Apoptosis in Leukemia Cells is Accompanied by Alterations in the Levels and Localization of Nucleolin," *J. Biol. Chem.* 278(10):8572-8579.
Nelson et al. (Jan. 5, 2006) "Fast Chromatin Immunoprecipitation Assay," *Nuc. Acids Res.* 34(1):e2-.
Prous Science (2005) "CX-3543, 286705," Annual Drug Data Report, 27(4):379.
Prous Science (Jul. 22, 2005) "Cx-2543 Begins Phase I Cancer Trial," Database Accession No. 386705. Retrieved from http://Integrity.prous.com.
Rangan et al. (Feb. 16, 2001) "Induction of Duplex to G-Quadruplex Transition in the c-*myc* Promoter Region by a Small Molecule," *J. Biol. Chem.* 276(7):4640-4646.

(Continued)

*Primary Examiner* — Shirley V Gembeh
(74) *Attorney, Agent, or Firm* — Lathrop & Gage LLP

(57) ABSTRACT

Provided is a method for improving treatment of a neoplastic condition by combining a therapeutically effective amount of a polyADP-ribose polymerase inhibitor with a therapeutically effective amount of a compound which triggers the release of nucleolin from the G-quadruplexes in rDNA. As specifically exemplified, the compound which increases nucleolin binding is a substituted quinobenzoxazine analog, for example CX-3543.

3 Claims, 2 Drawing Sheets

OTHER PUBLICATIONS

Rice et al. (Apr. 2005) "Design of CX-3543, a Novel Multi-Targeting Antitumor Agent," *Proc. Ann. Meet. Am. Assoc. Cancer Res.* 46:594, Abstract.

Seenisamy et al. (Published Online Feb. 5, 2005) "Design and Synthesis of an Expanded Porphyrin that has Selectivity for the c-MYC G-Quadruplex Structure," *J. Am. Chem. Soc.* 127(9):2944-2959.

Shiokawa et al. (Aug. 11, 1997) "Inhibitors of Poly(ADP-ribose) Polymerase Suppress Nuclear Fragmentation and Apoptotic-Body Formation During Apoptosis in HL-60 Cells," *FEBS Lett.* 413(1):99-103.

Siddiqui-Jain et al. (Sep. 3, 2002) "Direct Evidence for a G-Quadruplex in a Promoter Region and its Targeting with a Small Molecule to Repress c-*MYC* Transcription," *Proc. Nat. Acad. Sci. USA* 99(18):11593-11598.

Valeriote et al. (Sep. 1975) "Synergistic Interaction of Anticancer Agents: A Cellular Perspective," *Cancer Chemother. Rep.* 59(5):895-900.

Ying et al. (Feb. 11, 2000) "Nucleolin, A Novel Partner for the Myb Transcription Factor Family that Regulates their Activity," *J. Biol. Chem.* 275(6):4152-4158.

\* cited by examiner

COMBINATION CANCER CHEMOTHERAPY

CROSS REFERENCE TO RELATED APPLICATIONS

This application is a 371 application of PCT US2007/068601, filed May 9, 2007, which claims benefit of U.S. Provisional Application 60/800,824, filed May 16, 2006.

ACKNOWLEDGEMENT OF FEDERAL RESEARCH SUPPORT

This invention was made with funding from the National Institutes of Health (R01 CA094166). The United States government has rights in this invention.

BACKGROUND OF THE INVENTION

The present invention relates to compositions and methods depending on a combination of therapeutic agents for the treatment of cancer, specifically the combination of a G-quadruplex-interactive compound that binds to G-quadruplexes in rDNA to release the nucleolin already bound to these G-quadruplexes with a PARP inhibitor. This results in an increase in apoptosis.

SUMMARY

The present disclosure provides an improved method of treating cancer using a combination of a G-quadruplex-interactive compound that binds to G-quadruplexes in rDNA to release the nucleolin already bound to these G-quadruplexes together with a PARP inhibitor. This results in an increase in apoptosis in cancer cells. The PARP inhibitor can be administered to a patient (human or animal) in need of cancer treatment simultaneously or from 0.1 to 24 hours prior to or 0.1 to 24 after the administration of the G-quadruplex-interactive agent that releases the nucleolin bound to the G-quadruplex and triggers enhanced apoptosis of cancer cells, or the PARP inhibitor and the enhancer of nucleolin binding can be administered simultaneously, with each agent being administered in an amount sufficient to inhibit the growth and/or cell division of cancer (neoplastic) cells, and preferably to cause cancer cell death. In the methods provided herein, the PARP inhibitor can be benzamide (as specifically exemplified) or it can be 3-benzamide, 3-methoxybenzamide, carba-NAD$^+$, nicotinamide, a dihydroisoquinolinone, an isoquinolinone such as 5-methyl-dihydroisoquinolinone, a benzimidazole-4-carboxamide, a 2-aryl-benzimidazole-4-carboxamide, a benzoxazole-4-carboxamide, an N,N-dimethylaminomethyl, pyrrolidinomethyl or bis-benzamide derivative, for example 1,5-di(3-carbamoylphenyl)aminocarbonyloxy)pentane, a phthalazinone, a quinazolinone, an isoindolinone, a phenanthridinone, among others. The G-quadruplex-interactive agent that releases nucleolin from the rDNA bound to the G-quadruplexes and triggers apoptosis of cancer cells is desirably a substituted quinobenzoxazine analog; in an embodiment of the invention, it is CX-3543

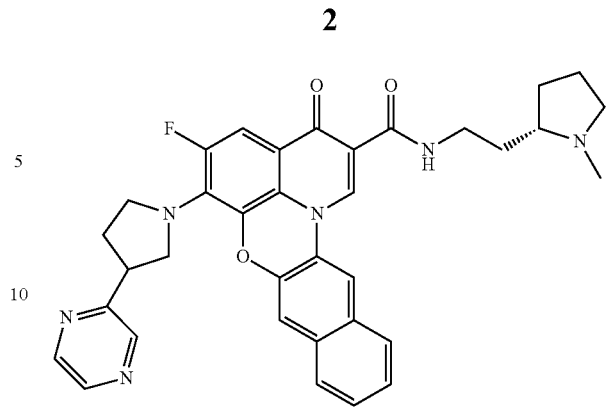

(see also US Patent Publication 2006-0029950, which is incorporated by reference herein). CX-3543 is a 50:50 mixture of RS and SS isomers. This combination chemotherapy can be administered in a single dose, or it can be administered at intervals chosen by a medical or veterinary practitioner.

The present disclosure further provides compositions comprising a PARP inhibitor and a G-quadruplex-interactive compound that triggers the release of nucleolin from the G-quadruplexes in the rDNA and triggers apoptosis of cancer cells. The compositions desirably further comprises a pharmaceutically acceptable excipient, especially one which is compatible with intravenous administration in human patients. In an embodiment of the invention, the composition comprises benzamide and CX-3543.

DETAILED DESCRIPTION

Figure 1B:
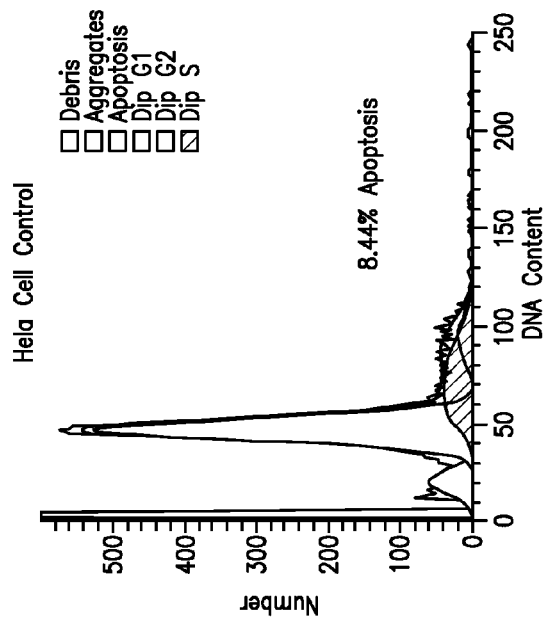
FIGS. 1A-1E show the results of FAScan analysis after HeLa cells were incubated with and without 1 mM benzamide for 30 minutes, followed by CX-3543 (1.0 µM) for 6 hours (FIG. 1D). The results for cells treated only with benzamide (FIG. 1C) and cells treated only with CX-3543 (FIG. 1E). Cells treated with staurosporine (FIG. 1A) served as a positive control for the induction of apoptosis and untreated cells (FIG. 1B) served as a negative control. Cells were harvested, washed once with PBS and resuspended in Krishan's buffer containing 0.05 mg/mL propidium iodide. Cells were vortexed 30 seconds and stored at 4° C. in the dark until they were analyzed by fluorescence activated flow cytometry (FACScan, BD BioSciences). Data were analyzed using ModFit software.
Figure 1C:
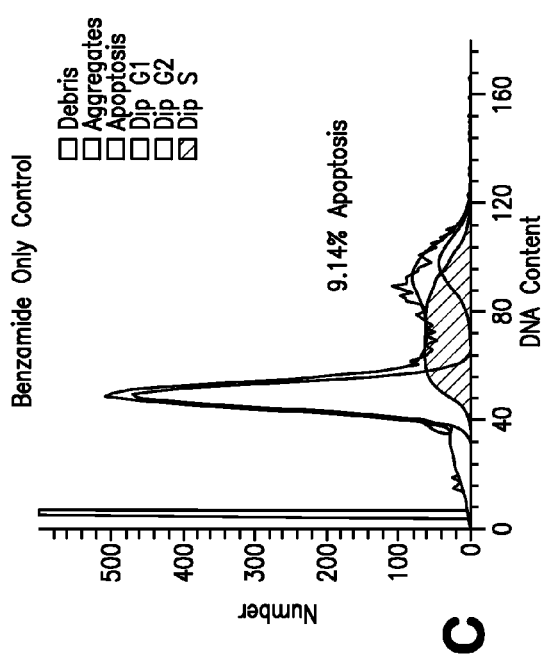
Figure 1A:
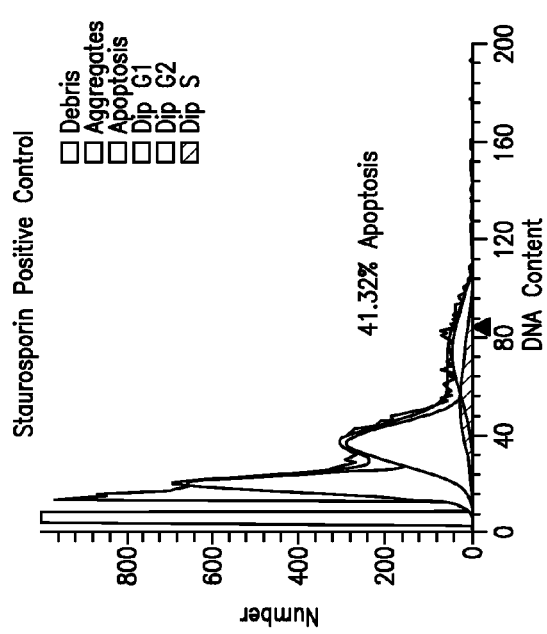
Figure 1E:
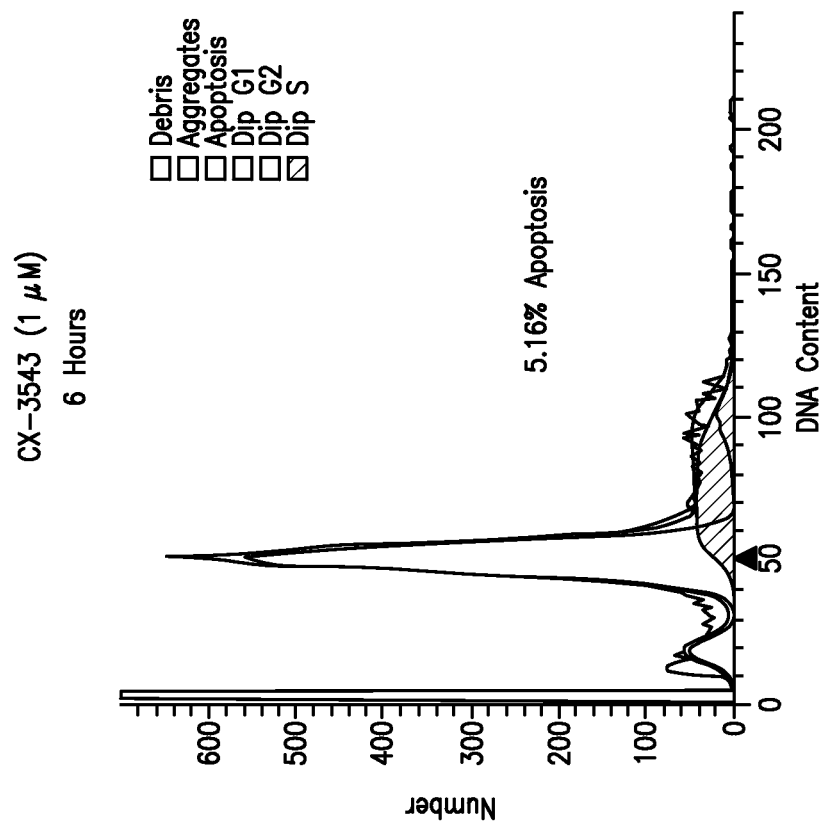
Figure 1D:
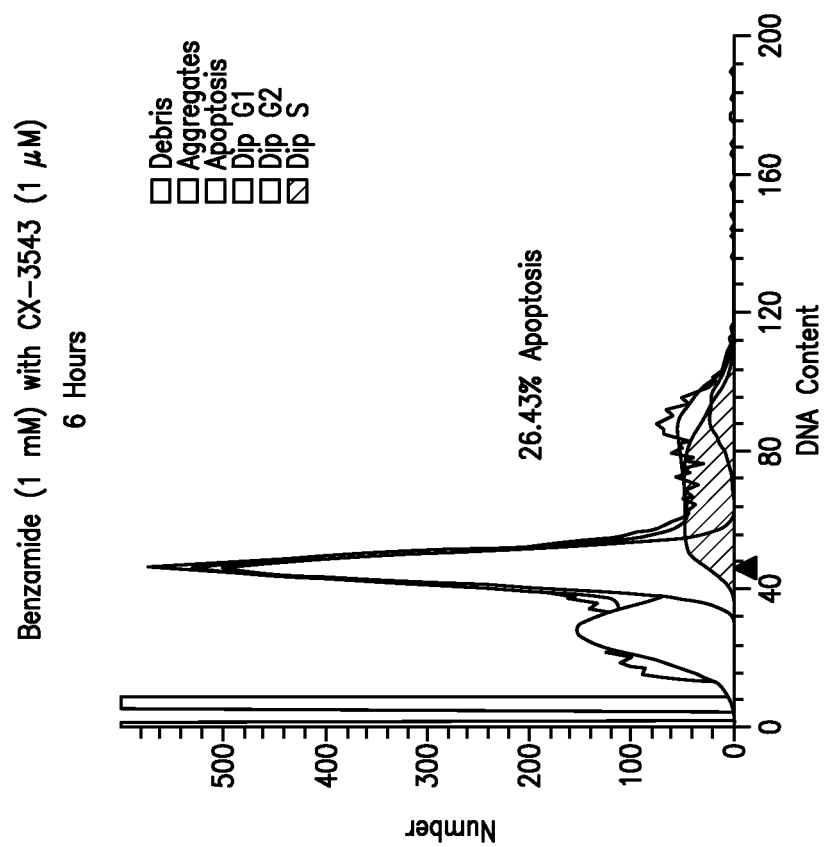

In the present context, a "PARP inhibitor" is a compound which inhibits the enzymatic activity of the enzyme poly-ADP-ribose polymerase in vivo and in vitro. Examples include 3-benzamide, 3-methoxybenzamide, carba-NAD$^+$, nicotinamide, didhydroisoquinolinones, isoquinolinones such as 5-methyl-dihydroisoquinolinone, benzimidazole-4-carboxamides, 2-aryl-benzimidazole-4-carboxamides, benzoxazole-4-carboxamides, N,N-dimethylaminomethyl, pyrrolidinomethyl and bis-benzamide derivatives, for example 1,5-di(3-carbamoylphenyl)aminocarbonyloxy)pentane, phthalazinones, quinazolinones, isoindolinones, and phenanthridinones, among others.

For the methods and therapeutic compositions provided herein, a PARP inhibitor is not toxic to humans (or animals) in the amounts used for chemotherapy of a neoplastic condition. In an embodiment of the invention, the PARP inhibitor is benzamide. Other PARP inhibitors are disclosed in Cepeda et al. (2006) Recent patents on Anti-Cancer Drug Discovery 1:39-53.

The G-quadruplex-interactive agent that triggers the release of nucleolin from the G-quadruplexes in rDNA and triggers apoptosis of cancer cells is desirably a substituted quinobenzoxazine analog. In an embodiment, it is CX-3543, the structure and synthesis of which is described in US Patent Publication 2006-0029950, which is incorporated by reference herein. The structure given is

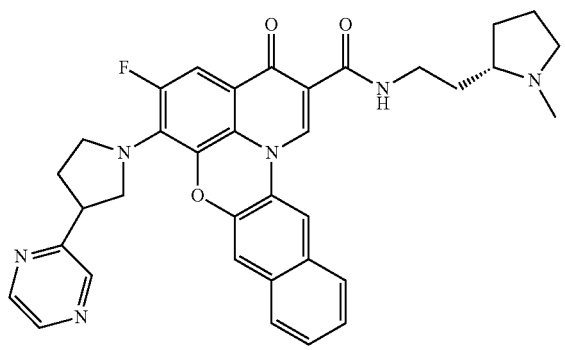 [SMILES: CN1CCC[C@H]1CCNC(=O)c1cn2c3c(c(N4CCC(c5cnccn5)C4)c(F)cc3c1=O)Oc1cc3ccccc3cc1-2]

As used herein, neoplasia means a disease state of a human or an animal in which there are cells and/or tissues which proliferate abnormally. Neoplastic conditions include, but are not limited to, cancers, sarcomas, tumors, leukemias, lymphomas, and the like. A neoplastic condition refers to the disease state associated with the neoplasia. Prostate cancer is an example (non-limiting) of a neoplastic condition.

The terms "treat," "treatment" and "therapeutic effect" as used herein refer to reducing or stopping a cell proliferation rate (e.g., slowing or halting tumor growth) or reducing the number of proliferating cancer cells (e.g., removing part or all of a tumor).

As used herein, the term "G-quadruplex-interactive agent" refers to a therapeutic agent that may be used for treating or ameliorating a cell proliferative disorder such as tumors or cancer.

As used herein, the term "apoptosis" refers to an intrinsic cell self-destruction or suicide program. In response to a triggering stimulus, cells undergo a cascade of events including cell shrinkage, blebbing of cell membranes and chromatic condensation and fragmentation. These events culminate in cell conversion to clusters of membrane-bound particles (apoptotic bodies), which are thereafter engulfed by macrophages.

In an embodiment of the invention, the trigger of nucleolin release from the G-quadruplexes in rDNA is (CX-3543), and other compounds with similar activity including without limitation, US Patent Publication 2006-0029950 for further information concerning this class of compound. Nucleolin release from the rDNA G-quadruplex can be measured using methods known to the art, for example, measuring bound nucleolin using a ChIP assay and nucleolin-specific antibody and chromatin from control cells and cells not treated with such a trigger, and noting from a 10% to greater than 90% nucleolin bound.

All art-known functional equivalents of methods, pharmaceutical formulations and delivery methods are intended to be included within the scope of the present invention. Whenever a range is given in the specification, for example, a temperature range, a time range, dosage range, concentration range, or a composition range, all intermediate ranges and subranges, as well as all individual values included in the ranges given are specifically included within the scope of the present invention.

Formulation of Compounds

As used herein, the term "pharmaceutically acceptable salts, esters and amides" includes but are not limited to carboxylate salts, amino acid addition salts, esters and amides of the compounds, as well as the zwitterionic forms thereof, which are known to those skilled in the art as suitable for use with humans and animals. (See, e.g., Gerge, S. M., et al., "Pharmaceutical Salts," J. Pharm. Sci. (1977) 66:1-19, which is incorporated herein by reference.)

Any suitable formulation of the compounds described herein can be prepared. In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, a-ketoglutarate, and a-glycerophosphate. Suitable inorganic salts may also be formed, including hydrochloride, sulfate, nitrate, bicarbonate, and carbonate salts. Pharmaceutically acceptable salts are obtained using standard procedures well known in the art. For example, pharmaceutically acceptable salts may be obtained by reacting a sufficiently basic compound such as an amine with a suitable acid affording a physiologically acceptable anion. Alkali metal (e.g., sodium, potassium or lithium) or alkaline earth metal (e.g., calcium) salts of carboxylic acids also are made.

A compound may be formulated as a pharmaceutical composition and administered to an animal, especially a mammalian, patient in need of such treatment. In one embodiment, the mammalian host is human. Any suitable route of administration may be used, including but not limited to oral, parenteral, intravenous, intramuscular, topical and subcutaneous routes.

In one embodiment, a compound is administered systemically (e.g., orally) in combination with a pharmaceutically acceptable vehicle such as an inert diluent or an assimilable edible carrier. They may be enclosed in hard or soft shell gelatin capsules, compressed into tablets, or incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may be varied and may conveniently be between about 2 to about 60% of the weight of a given unit dosage form. The amount of active compound in such therapeutically useful compositions is such that an effective dosage level will be obtained.

Tablets, troches, pills, capsules, and the like also may contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Any material used in preparing any unit dosage form is pharmaceutically acceptable and substantially non-toxic in the amounts employed. In addition, the active compound may be incorporated into sustained-release preparations and devices.

The active compound also may be administered intravenously or intraperitoneally by infusion or injection. Solutions of the active compound or its salts may be prepared in a buffered solution, often phosphate buffered saline, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms. The compound is sometimes prepared as a polymatrix-containing formulation for such administration (e.g., a liposome or microsome). Liposomes are described for example in U.S. Pat. No. 5,703, 055 (Felgner, et al.) and Gregoriadis, Liposome Technology vols. I to III (2nd ed. 1993).

The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in liquid form. Compounds often are administered as compositions or formulations, in combination with a dermatologically acceptable carrier, which may be a solid or a liquid. Examples of useful dermatological compositions used to deliver compounds to the skin are known (see, e.g., Jacquet, et al. (U.S. Pat. No. 4,608,392), Geria (U.S. Pat. No. 4,992,478), Smith, et al. (U.S. Pat. No. 4,559,157) and Wortzman (U.S. Pat. No. 4,820,508).

Therapeutic compounds may be formulated with a solid carrier, which include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Generally, the concentrations of the compounds in a liquid composition often is from about 0.1 wt % to about 25 wt %, sometimes from about 0.5 wt % to about 10 wt %. The concentration in a semi-solid or solid composition such as a gel or a powder often is about 0.1 wt % to about 5 wt %, sometimes about 0.5 wt % to about 2.5 wt %. A compound composition may be prepared as a unit dosage form, which is prepared according to conventional techniques known in the pharmaceutical industry. In general terms, such techniques include bringing a compound into association with pharmaceutical carrier(s) and/or excipient(s) in liquid form or finely divided solid form, or both, and then shaping the product if required.

Table 3 of US Patent Publication 2006-0029950 shows various formulations for use with compounds described herein. For example, the compound CX-3543 may be formulated having dosages from 10 mg/mL to 20 mg/mL solution, using the formulations herein. "D5W" refers to deionized water with 5% dextrose. Each component in each formulation may be varied without affecting the activity of the compound. In one example, the compound is formulated in a solution comprising polyethylene glycol and propylene glycol in a buffer solution such as a phosphate buffer. The concentration of polyethylene glycol may be between 5% (w/w) and 10% (w/w); and the concentration of propylene glycol may be in between 6% (w/w) and 12% (w/w).

The compound composition may be formulated into any dosage form, such as tablets, capsules, gel capsules, liquid syrups, soft gels, suppositories, and enemas. The compositions also may be formulated as suspensions in aqueous, non-aqueous, or mixed media. Aqueous suspensions may further contain substances which increase viscosity, including for example, sodium carboxymethylcellulose, sorbitol, and/or dextran. The suspension may also contain one or more stabilizers.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

Dosages

A useful compound dosage often is determined by assessing its in vitro activity in a cell or tissue system and/or in vivo activity in an animal system. For example, methods for extrapolating an effective dosage in mice and other animals to humans are known to the art (see, e.g., U.S. Pat. No. 4,938, 949). Such systems can be used for determining the $LD_{50}$ (the dose lethal to 50% of the population) and the $ED_{50}$ (the dose therapeutically effective in 50% of the population) of a compound. The dose ratio between a toxic and therapeutic effect is the therapeutic index and it can be expressed as the ratio $ED_{50}/LD_{50}$. The compound dosage often lies within a range of circulating concentrations for which the $LD_{50}$ is associated with little or no toxicity. The dosage may vary within this range depending upon the dosage form employed and the route of administration utilized. For any compounds used in the methods described herein, the therapeutically effective dose can be estimated initially from cell culture assays. A dose sometimes is formulated to achieve a circulating plasma concentration range covering the $IC_{50}$ (i.e. the concentration of the test compound which achieves a half-maximal inhibition of symptoms) as determined in in vitro assays, as such information often is used to more accurately determine useful doses in humans. Levels in plasma may be measured, for example, by high performance liquid chromatography.

Another example of effective dose determination for a subject is the ability to directly assay levels of "free" and "bound" compound in the serum of the test subject. Such assays may utilize antibody mimics and/or "biosensors" generated by molecular imprinting techniques. The compound is used as a template, or "imprinting molecule", to spatially organize polymerizable monomers prior to their polymerization with catalytic reagents. Subsequent removal of the imprinted molecule leaves a polymer matrix which contains a repeated "negative image" of the compound and is able to selectively rebind the molecule under biological assay conditions (see, e.g., Ansell, et al., Current Opinion in Biotechnology (1996) 7:89-94 and in Shea, Trends in Polymer Science (1994) 2:166-173). Such "imprinted" affinity matrixes are amenable to ligand-binding assays, whereby the immobilized monoclonal antibody component is replaced by an appropriately imprinted matrix (see, e.g., Vlatakis, et al., Nature (1993) 361:645-647). Through the use of isotope-labeling, "free" concentration of compound can be readily monitored and used in calculations of $IC_{50}$. Such "imprinted" affinity matrixes can also be designed to include fluorescent groups whose photon-emitting properties measurably change upon local and selective binding of compound. These changes can be readily assayed in real time using appropriate fiberoptic devices, in turn allowing the dose in a test subject to be quickly optimized based on its individual $IC_{50}$. An example of such a "biosensor" is discussed in Kriz, et al., Analytical Chemistry (1995) 67:2142-2144.

Exemplary doses include milligram or microgram amounts of the compound per kilogram of subject or sample weight, for example, about 1 microgram per kilogram to about 500 milligrams per kilogram, about 100 micrograms per kilogram to about 5 milligrams per kilogram, or about 1 microgram per kilogram to about 50 micrograms per kilogram. It is understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid described herein, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The exact formulation, route of administration and dosage of a PARP inhibitor, to be administered prior to or together with the trigger of nucleolin release from the G-quadruplexes in rDNA, such as CX-3543, can be chosen by the individual physician in view of the patient's condition (see e.g. Fingl et al., in The Pharmacological Basis of Therapeutics, 1975, Ch. 1 p. 1).

It should be noted that the attending physician knows how to and when to terminate, interrupt, or adjust dose and/or schedule due to toxicity, organ dysfunctions, or successful treatment, as evidence by tumor regression, decrease in blood levels of a relevant cancer marker, lessened pain, or the like. Conversely, the attending physician also knows to adjust treatment to higher levels if the clinical response is not adequate (precluding toxicity). The magnitude of an administered dose in the management of the disorder of interest varies with the severity of the condition to be treated and to the route of administration. The severity of the condition may, for example, be evaluated, at least in part, by standard prognostic evaluation methods. Further, the dose and/or dose frequency, also vary according to the age, body weight, and particular response of the individual patient. Similar considerations apply to veterinary medicine as well.

Depending on the specific conditions being treated and the targeting method selected, a therapeutic composition comprising a PARP inhibitor or a PARP inhibitor together with a trigger of nucleolin release of the G-quadruplexes in rDNA as the active ingredient(s) may be formulated and administered systemically or locally, for example, topically. Techniques for formulation and administration are well known to the art. Suitable routes can include, for example, topical, oral, rectal, transdermal, vaginal, transmucosal, or intestinal administration; parenteral delivery, including intramuscular, subcutaneous, or intramedullary injections, as well as intrathecal, intravenous, or intraperitoneal injections.

For injection, the therapeutic agent may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art. Topical formulations are also well known to the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular those formulated as solutions, may be administered parenterally, such as by intravenous injection. Appropriate compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes and then administered as described above. Liposomes are spherical particles with aqueous interiors bounded lipid bilayers. Soluble molecules present in an aqueous solution at the time of liposome formation are incorporated into the aqueous interior. The liposomal contents are both protected from the external microenvironment and, because liposomes fuse with cell membranes, the contents are efficiently delivered into the cell cytoplasm. Additionally, due to their hydrophobicity, small organic molecules may be directly administered intracellularly.

Pharmaceutical compositions suitable for use in the present invention include compositions wherein the combination of PARP inhibitor and trigger of nucleolin release from the G-quadruplexes in rDNA, is present in an effective amount to achieve the intended purpose, i.e., of ameliorating a neoplastic condition in a patient, especially, a cancerous condition. Determination of the effective amount(s) is well within the capability of those skilled in the art.

In addition to the active ingredients, these pharmaceutical compositions may contain suitable pharmaceutically acceptable carriers including excipients and auxiliaries which facilitate processing of the active compounds into preparations which can be used pharmaceutically. The preparations formulated for oral administration may be in the form of tablets, dragees, capsules, or solutions, including those formulated for delayed release or only to be released when the pharmaceutical reaches the small or large intestine, as necessary.

The pharmaceutical composition(s) of the present invention may be manufactured by any means known to the art, including but not limited to, conventional mixing, dissolving, granulating, dragee-making, levitating, emulsifying, encapsulating, entrapping or lyophilizing processes.

Pharmaceutical formulations for parenteral administration include aqueous solutions of the. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. The frequency of dosing depends on the disease treated. Neoplastic conditions including, but not limited to, blood cancers, leukemias), lymphomas, prostate cancer, breast cancer, uterine cancer, ovarian cancer, colon cancer, bone cancer, melanoma, squamous cell cancer, basal cell cancer, among others, can be treated with CX-3543 together with a PARP inhibitor, simultaneously administered or sequentially administered in any order, with the administration at intervals and in amounts effective for limiting the growth and cell division of neoplastic cells and/or causing neoplastic cell death. Repeated administrations at intervals deemed appropriate can be determined by the physician or veterinarian. An example of an administration strategy would be daily simultaneous administrations for five days, followed by 2-3 weeks rest period, with further dosing schedules as judged appropriate.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

All references cited herein are incorporated by reference herein to the extent there is no inconsistency with the present disclosure. The references cited herein reflect the level of skill in the relevant arts.

Although the description herein contains certain specific information, it should not be construed as limiting the scope of the invention but as merely providing illustrations of some of the presently preferred embodiments of the invention. For example, thus the scope of the invention should be determined by the appended claims and their equivalents, rather than by the examples given.

As used herein, "comprising" is synonymous with "including," "containing," or "characterized by," and does not exclude additional, unrecited elements or method steps. As used herein, "consisting of" excludes any element, step, or ingredient not specifically recited. As used herein, "consisting essentially of" does not exclude materials or steps that do not materially affect the basic and novel characteristics of the claim. Any recitation herein of the term "comprising", particularly in a description of components of a composition or in a description of elements of a device, encompasses those compositions and methods consisting essentially of and consisting of the recited components, elements or steps. The invention illustratively described herein suitably may be practiced in the absence of any element or elements, limitation or limitations which is not specifically disclosed herein.

The terms and expressions which have been employed herein are used as terms of description and not of limitation, and there is no intent to exclude any equivalents of the features shown and described or portions thereof, and it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A method for improving the chemotherapeutic effect of a substituted quinobenzoxazine analog which triggers the release of nucleolin from G-quadruplexes in rDNA, said method comprising the step of combining said compound with an effective amount of a second compound which inhibits the activity of polyADP-ribose polymerase (PARP), wherein the substituted quinobenzoxazine analog is CX-3543, characterized by the chemical structure

11

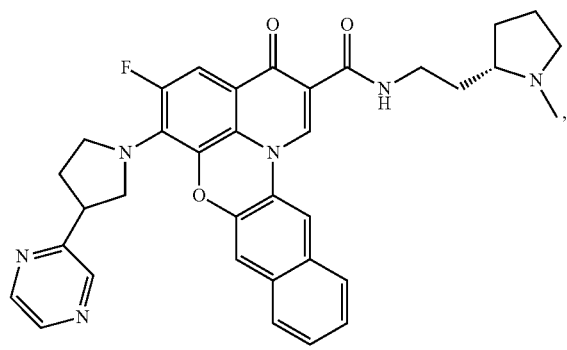 [SMILES: CN1CCC[C@H]1CCNC(=O)c1cn2c3c(c(N4CCC(c5cnccn5)C4)c(F)cc3c1=O)Oc1cc3ccccc3cc1-2 ; ","]

12

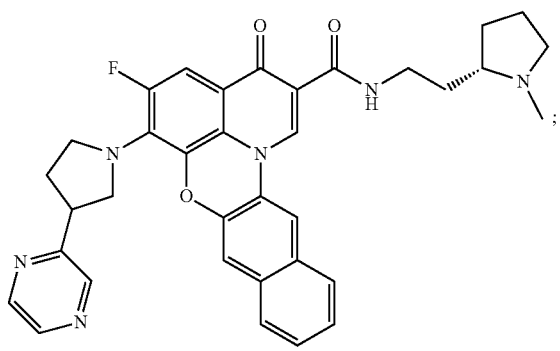 [SMILES: CN1CCC[C@H]1CCNC(=O)c1cn2c3c(c(N4CCC(c5cnccn5)C4)c(F)cc3c1=O)Oc1cc3ccccc3cc1-2]

and wherein the second compound is benzamide or a pharmaceutically acceptable salt of one of the recited compounds.

2. A method of treating a neoplastic condition in a patient in need thereof, said method comprising the step of administering a substituted quinobenzoxazine analog which results in the release of nucleolin from G-quadruplexes in rDNA), wherein the substituted quinobenzoxazine analog is CX-3543, characterized by the chemical structure and the step of administering an effective amount of a second compound which inhibits the activity of polyADP-ribose polymerase (PARP), wherein the second compound is benzamide or a pharmaceutically acceptable salt of one of the recited compounds, or in the reverse order or at the same time.

3. The method of claim 2, wherein the first and second compound are simultaneously administered.

* * * * *

UNITED STATES PATENT AND TRADEMARK OFFICE
CERTIFICATE OF CORRECTION

PATENT NO.       : 8,481,529 B2                                                      Page 1 of 1
APPLICATION NO. : 12/301217
DATED            : July 9, 2013
INVENTOR(S)      : Hurley et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 690 days.

Signed and Sealed this
Eighth Day of September, 2015

Michelle K. Lee
*Director of the United States Patent and Trademark Office*